US007715990B2

(12) United States Patent
Zou et al.

(10) Patent No.: US 7,715,990 B2
(45) Date of Patent: May 11, 2010

(54) PROBE CORRECTION FOR GENE EXPRESSION LEVEL DETECTION

(75) Inventors: Guangzhou Zou, San Diego, CA (US); Hur-Song Chang, San Diego, CA (US); Yiping Fan, San Diego, CA (US); Fan Long, Bridgewater, NJ (US); Xun Wang, Chapel Hill, NC (US); Tong Zhu, Chapel Hill, NC (US)

(73) Assignee: Syngenta Participations AG, Basel (CH)

( * ) Notice: Subject to any disclaimer, the term of this patent is extended or adjusted under 35 U.S.C. 154(b) by 664 days.

(21) Appl. No.: 10/500,587

(22) PCT Filed: Jan. 17, 2003

(86) PCT No.: PCT/US03/01636

§ 371 (c)(1),
(2), (4) Date: Oct. 21, 2004

(87) PCT Pub. No.: WO03/062450

PCT Pub. Date: Jul. 31, 2003

(65) Prior Publication Data

US 2005/0064426 A1    Mar. 24, 2005

Related U.S. Application Data

(60) Provisional application No. 60/349,874, filed on Jan. 18, 2002.

(51) Int. Cl.
*G01N 33/483* (2006.01)

(52) U.S. Cl. .................................. 702/20; 435/6

(58) Field of Classification Search ........................ None
See application file for complete search history.

(56) References Cited

U.S. PATENT DOCUMENTS

| 5,830,645 | A  | * | 11/1998 | Pinkel et al. | .............. | 435/6 |
| 6,309,822 | B1 | * | 10/2001 | Fodor et al. | .............. | 435/6 |
| 2003/0182066 | A1 | | 9/2003 | Konishi | | |
| 2007/0037144 | A1 | * | 2/2007 | Wohlgemuth et al. | .......... | 435/6 |

OTHER PUBLICATIONS

Tseng et al (NAR, vol. 29, No. 12, p. 2549-2557, 2001).*
Jelinsky et al. (Mol. Cell. Biol., vol. 20, No. 21, p. 8157-8167, Nov. 2000).*
Pietu et al. (Genome Research, vol. 6, p. 492-503, 1996).*
Kincaid et al. (Information Visualization, vol. 4, p. 176-190, 2005).*
Colantuoni et al., "SNOMAD (Standardization and Normalization of MicroArray Data): web-accessible gene expression data analysis", Bioinformatics. Apr. 2002, vol. 18, No. 11, pp. 1540-1541.
Yang et al., "A statistical method for flagging weak spots improves normalization and ration estimates in microarrays", Physiological Genomics, Aug. 2001, vol. 7, pp. 45-53.
Kerr et al., "Analysis of Variance for Gene Expression Microarray Data", Journal of Computational Biology, 2000, vol. 7, No. 6, pp. 819-837.
Office Communication corresponding to the European Patent Application No. 03705827.8-2402 dated Jun. 27, 2007.
Claverie, Jean-Michel. Computational methods for the indentification of differential and coordinated gene expression. *Human Molecular Genetics*, vol. 8, No. 10, (1999), pp. 1821-1832.
Selinger et al. RNA expression analysis using a 30 base pair resolution *Escherichia coli* genome array. *Nature Biotechnology*, vol. 18, (2000), pp. 1262-1268.
Talaat et al. Genome-directed primers for selective labeling of bacterial transcripts for DNA microarray analysis. *Nature Biotechnology*, vol. 18, (2000), pp. 679-682.
Schadt et al. Analyzing high-density oligonucleotide gene expression array data. *Journal of Cellular Biochemistry*, vol. 80, (2000), pp. 192-202.
Tseng et al. Issues in cDNA microarray analysis: quality filtering, channel normalization, models of variations and assessment of gene effects. *Nucleic Acids Research*, vol. 29, No. 12, (2001), pp. 2549-2557.
Tallat et al. Genomic DNA standards for gene expression profiling in *Mycobacterium tuberculosis*. *Nucleic Acids Research*, vol. 30, No. 20, (2002), pp. e104.
Office Communication corresponding to the Australian Patent Application No. 2003207611 dated Jan. 2, 2007.
Yang et al., "A Statistical Method For Flagging Weak Spots Improves Normalization And Ratio Estimates In Microarrays," Physiol. Genomics, vol. 7, pp. 45-53 (2001).
Official Action corresponding to Japanese Patent Application No. 2003-562317 dated Aug. 26, 2008. (Translation).
Official Communication corresponding to Canadian Patent Application No. 2,472,733 dated Nov. 10, 2008.
Chudin et al. Assesment of the relationship between signal intensities and transcript concentration for Affuymetrix GeneChip® arrays. *Genome Biology*, vol. 3, No. 1, pp. 1-10, 2001.

* cited by examiner

*Primary Examiner*—Karlheinz R Skowronek
(74) *Attorney, Agent, or Firm*—Bruce Vrana

(57) ABSTRACT

Individual probes on micro-arrays are re-scaled and corrected with a set of probe dependent coefficients derived from genomic-DNA hybridization signals. A dynamic range for gDNA binding is determined by measuring a concentration signal curve. Signals for each probe are measured during multiple hybridizations within a linear range. Concentration insensitive probes are then found for two sets of experiments. Probes are discarded based on a threshold compared to their standard deviation divided by their average in each set. The correction coefficients are used to calculate a corrected intensity for each probe. Probes having high uncertainty (0.5 in one embodiment) are discarded. A weighting factor for each probe is determined along with an uncertainty factor. Finally, a call for each gene is made, such as absent, marginal or present.

26 Claims, 4 Drawing Sheets

210 — CALCULATE THE CORRECTED SIGNAL VALUE ON A PROBE. THE CORRECTED SIGNAL FOR A PROBE CAN BE CALCULATED AS
$$S_i^{corrected} = c_i S_i$$
WHERE $S$ IS THE OBSERVED SIGNAL ON PROBE i.

220 — CALCULATE THE WEIGHTING FACTOR FOR A PROBE. IF $m(>=1)$ OLIGOS ARE USED TO DETECT THE EXPRESSION LEVEL OF ONE GENE, THE WEIGHTING FACTOR FOR THE iTH OLIGO CAN BE CALCULATED AS:
$$w_i = \frac{d_i}{\sum_{l}^{m} d_l}$$
WHERE $d$ IS THE UNCERTAINTY COEFFICIENT. IN THE CASE WHERE ONLY ONE OLIGO IS USED TO REPRESENT A GENE (m=1), THEN THE WEIGHTING FACTOR w EQUALS TO 1.0.

230 — CALCULATE THE EXPRESSION LEVEL FOR A GENE. THE WEIGHTING FACTOR CAN BE USED TO CALCULATE THE EXPRESSION VALUE FOR A GENE. FOR EXAMPLE, IN THE SIMPLEST CASE, THE EXPRESSION OF A GENE CAN BE CALCULATED AS:
$$v = \frac{1}{m} \sum_{i=1}^{m} w_i S_i^{corrected}$$
WHERE v IS THE EXPRESSION VALUE AND $m$ IS THE NUMBER OF THE PROBES USED TO DETECT THE GENE.

240 — CALCULATE THE UNCERTAINTY OF THE GENE EXPRESSION LEVEL D:
$$D = \frac{1}{m} \sum_{i=1}^{m} d_i S_i^{corrected}$$

250 — CONVERT THE CORRECTED SIGNAL TO THE NUMBER OF COPY PER CELL. IN THE CASE WHEN THE NUMBER OF COPY PER CELL VALUE IS KNOWN FOR ONE GENE, WE CAN CONVERT THE MEASUREMENTS OF ALL OTHER GENES TO THE NUMBER OF COPY PER CELL VALUES. LET $n0$ BE THE NUMBER OF COPIES PER CELL FOR GENE 0. IF $n0$ IS KNOWN, WE CAN OBTAIN THE NUMBER OF COPIES PER CELL VALUE FOR ANY OTHER GENE $\alpha$ AS:
$$n_\alpha = \frac{S_\alpha^{corrected}}{S_0^{corrected}} n_0$$
THE VALUE WILL THUS BECOME TECHNOLOGY INDEPENDENT.

Figure 2

210 — CALCULATE THE CORRECTED SIGNAL VALUE ON A PROBE. THE CORRECTED SIGNAL FOR A PROBE CAN BE CALCULATED AS $$S_i^{corrected} = c_i S_i$$

WHERE $S$ IS THE OBSERVED SIGNAL ON PROBE i.

220 — CALCULATE THE WEIGHTING FACTOR FOR A PROBE. IF $m(>=1)$ OLIGOS ARE USED TO DETECT THE EXPRESSION LEVEL OF ONE GENE, THE WEIGHTING FACTOR FOR THE iTH OLIGO CAN BE CALCULATED AS:

$$w_i = \frac{1 - \alpha^{d_i S_i^{cor} / \sum d_i S_i^{cor}}}{\sum (1 - \alpha^{d_i S_i^{cor} / \sum d_i S_i^{cor}})}$$

WHERE $d$ IS THE UNCERTAINTY COEFFICIENT. IN THE CASE WHERE ONLY ONE OLIGO IS USED TO REPRESENT A GENE (m=1), THEN THE WEIGHTING FACTOR w EQUALS TO 1.0.

230 — CALCULATE THE EXPRESSION LEVEL FOR A GENE. THE WEIGHTING FACTOR CAN BE USED TO CALCULATE THE EXPRESSION VALUE FOR A GENE. FOR EXAMPLE, IN THE SIMPLEST CASE, THE EXPRESSION OF A GENE CAN BE CALCULATED AS:

$$V_i = \sum_{i=1}^{m} w_i S_i^{cor}$$

WHERE v IS THE EXPRESSION VALUE AND $m$ IS THE NUMBER OF THE PROBES USED TO DETECT THE GENE.

240 — CALCULATE THE UNCERTAINTY OF THE GENE EXPRESSION LEVEL D:

$$D = \frac{1}{m} \sum_{i=1}^{m} d_i S_i^{corrected}$$

250

ENTER A USER-DEFINED THRESHOLD VALUE FOR Z.

CALCULATE A Z-SCORE.

CALCULATE A CALL FOR EACH GENE FROM THE THRESHOLD AND Z-SCORE VALUES

CALL=1     INDICATES PRESENCE OF TRANSCRIPT
CALL=0     INDICATES MARGINAL PRESENCE OF TRANSCRIPT
CALL=-1    INDICATES ABSENCE OF TRANSCRIPT

Figure 4

PROBE CORRECTION FOR GENE EXPRESSION LEVEL DETECTION

CROSS REFERENCE TO RELATED APPLICATIONS

This application claims the benefits of U.S. Provisional Application Ser. No. 60/349,874 filed Jan. 18, 2002, which is incorporated herein by reference in its entirety for all purposes.

FIELD OF THE INVENTION

The present invention relates to the field of detecting gene expression levels using probes, and in particular to correction of the probes and use of the corrected probes.

BACKGROUND OF THE INVENTION

Gene expression analysis is becoming more common now that sequence information for DNA is readily available. One way of obtaining information about genes involves the use of an array of probes. One type of probe is made on a silicon array of cells, consisting of DNA fragments or oligomers attached at each cell. The DNA probe is used to hybridize marked RNA transcripts, or more typically their cDNA counterparts, produced by a target gene. The DNA probe in the array is exposed to the RNA transcripts or cDNAs, which then attach or hybridize to the DNA probes if they match. Unattached RNAs or cDNAs are washed away, and the array is exposed to laser light causing the attached RNA associated fluorophores to fluoresce. The amount of fluorescence is measured and is representative of the expression level of the gene.

Millions of independent gene expression measurements are made each year using different probes. There are serious obstacles to accurately mining and systematically integrating the measurements. Since probes exhibit different sensitivities, it is difficult to compare results from different probes. Several problems are encountered, including how to compare expression levels between different genes, how to determine absolute expression values, and how to eliminate cross-hybridization signals. The present invention provides a means to overcome these difficulties.

SUMMARY OF THE INVENTION

Individual probes on micro-arrays are re-scaled and corrected with a set of probe dependent coefficients derived from genomic-DNA ("gDNA") hybridization signals. Multiple steps are performed to derive the coefficients. A dynamic range for gDNA binding is determined by measuring a concentration signal curve. Signals for each probe are measured during multiple hybridizations within a linear range.

Concentration insensitive probes are then found for two sets of experiments. Probes are discarded based on a threshold compared to their standard deviation divided by their average in each set. In one embodiment, the threshold for each set is different. The threshold for the sets varies between about 0.34 and 0.07. A correlation coefficient is used in further embodiments to discard probes. An intersection for discarded probes for the two sets is found and used to normalize probe intensities from different hybridizations globally.

An average and standard deviation is calculated for the hybridization signals observed on each oligo, and the correction coefficient for each oligo is calculated by requiring its signal average to be equal to a constant. An uncertainty coefficient is calculated for each oligo as the ratio between the standard deviation and average.

The correction coefficients are used to calculate a corrected intensity for each probe. Probes having high uncertainty (0.5 in one embodiment) are discarded. A weighting factor for each probe is determined along with an uncertainty factor. Finally, a call for each gene is made, such as absent, marginal or present. Probe intensities are normalized globally, and the correction coefficient is applied to each probe. The intensity of probes is compared, and a significance score is calculated for a corresponding gene. The score is used to make the call.

In one embodiment, an output is provided that includes elements selected from the group of gene identifiers, gene expression values both before and after correction, call for each gene, total probes, used probes, uncertainty, average, standard deviation and corrected intensity for each probe.

BRIEF DESCRIPTION OF THE DRAWINGS

FIG. 2 is a flowchart of a method of using the correction coefficients generated by the flowchart of FIG. 1.

FIG. 4 is a flowchart of an alternative method of using the correction coefficients generated by the flowchart of FIG. 1, including a call step.

DETAILED DESCRIPTION OF THE INVENTION

In the following description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural, logical and electrical changes may be made without departing from the scope of the present invention. The following description is, therefore, not to be taken in a limited sense, and the scope of the present invention is defined by the appended claims.

The detailed description describes how individual oligo probes on a micro-array are rescaled and normalized. A set of probe dependent coefficients are derived from genomic-DNA hybridization signals. Following derivation of the coefficients, a second part of the detailed description describes how they are used to make a call for each gene, such as absent, marginal or present. A simplified computer system for performing the above derivation and use of correction coefficients is also provided. A conclusion summarizes certain aspects of the invention and describes potential benefits depending on embodiments of the invention used. Pseudocode is embedded in the detailed description and represents methods that are performed either by a person, machine or computer. When implemented by computer, they represent software modules or other form of software. Functions may be implemented in individual modules, or combined into one or more modules.

Figure 1:
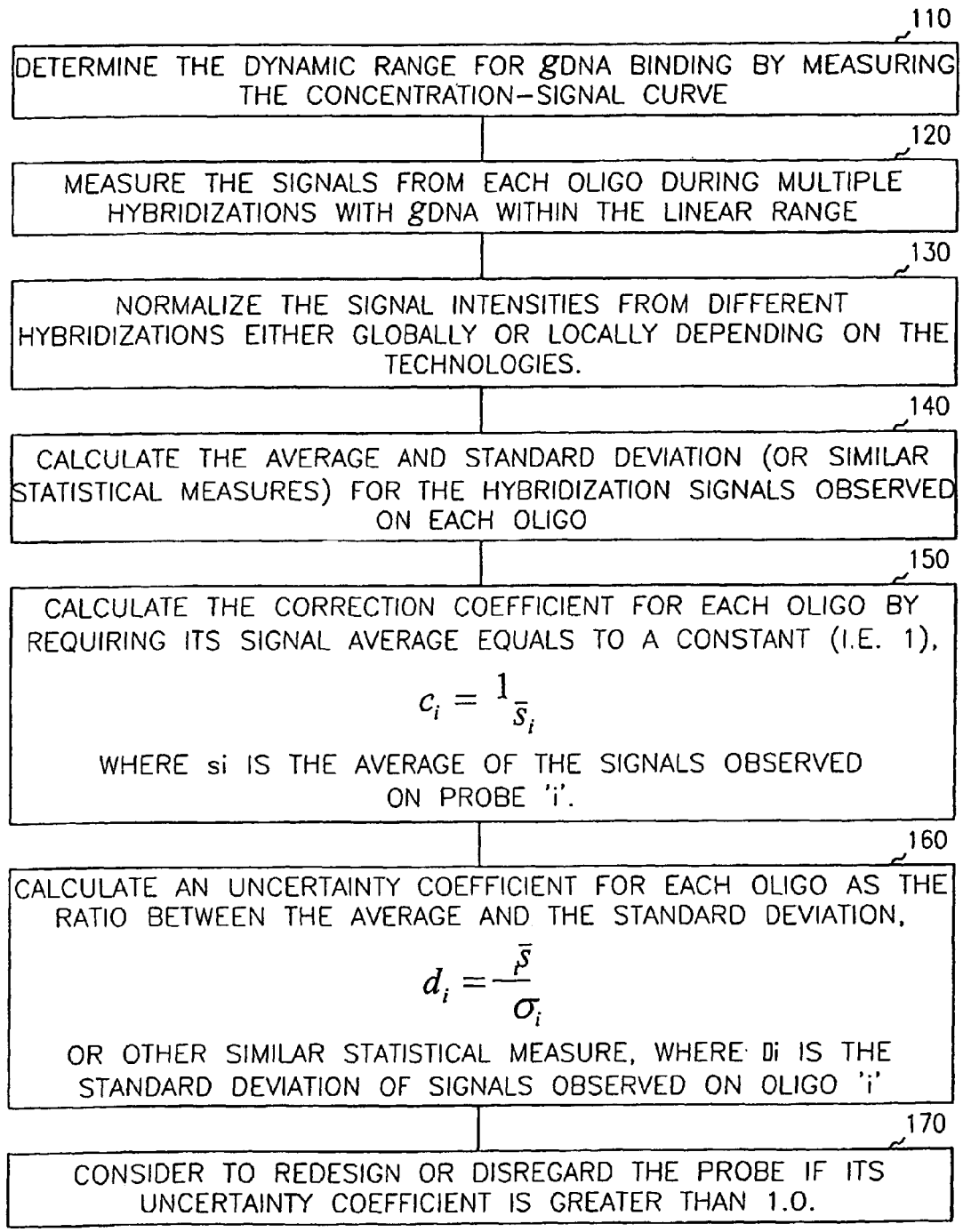
FIG. 1 is a flowchart of a method of generating correction coefficients for oligo probes.

Coefficient Derivation:

FIG. 1 is a simplified flowchart showing coefficient derivation.

Step 1. Determine the dynamic range for gDNA binding by measuring the concentration-signal curve at 110. (1, 2, 3, 4, 5, 6, 9, 15, and 24 micrograms gDNA were used in one embodiment)

Step 2. Measure the signals for each oligo during multiple hybridizations with gDNA within linear range at 120. (4, 5, and 6 micrograms were used, each having 3 replica chips)

Step 3. Find concentration insensitive probes and use the output of this step as an input for a normalization function at 130.

There are two sets of experiments:

Set one: 1, 2, 3, 6, and 9 micrograms; calculate average of gene expression for each chip. Calculate average (ave) and standard deviation (sd) of average gene expressions across all chips. Then calculate CV1=sd/ave=0.34

Set two: 4, 5, and 6 microgram, similar to set one, calculate CV2=sd/ave=0.14

Case1:

For each probe in set one, calculate its-ave and sd, then calculate CV=sd/ave. If CV<CV1(0.34), discard this probe. Pseudocode is used selectively in the following description.

```
cal_raw_ave_all_concern.pl
input:
1.discard_threshold(use 0.34)
2.all related intensity files in current directory
Format(5 columns)
Gene_name   Gene_number   probe_coordinate_x
probe_coordinate_y
probe_intensity
OUTPUT
Discard_threshold
Format:
Gene_name probe_coordinate_x probe_coordinate_y
```

For each probe in set two, calculate its ave and sd, then calculate CV=sd/ave

If CV<CV2(0.14), discard this probe
cal_raw_ave_all_concern.pl
same as above, but discard_threshold is 0.14

Get discarded probes from set-one and set-two, find their intersection, use it as an input of step 4, the other input of step 4 is a dummy input.

Total 16559 probes discarded in one embodiment.

Case2:

For each probe in set one, calculate its ave and sd, calculate CV=sd/ave

If CV<0.5*CV1(0.34*0.5=0.17), discard this probe
cal_raw_ave_all_concern.pl
same as above, but discard_threshold is 0.17

For each probe in set two, calculate its ave and sd, calculate CV=sd/ave

If CV<CV2*0.5(0.14*0.5=0.07)), discard this probe
cal_raw_ave_all_concern.pl
same as above, but discard_threshold is 0.07

Get discarded probe file from set1 and set2, use these two sets as inputs of step 4. (i.e. use the union of these two sets)

Total 10237 probes discarded in one embodiment.

Case3:

For each probe in set one, calculate its ave and sd, calculate CV=sd/ave

If CV<0.5*CV1(0.34*0.5=0.17), discard this probe

For each probe in set two, calculate its ave and sd, calculate CV=sd/ave

If CV<CV2*0.5(0.14*0.5=0.07)), discard this probe
cal_raw_ave_all_concern.pl
same as case2

Get discarded probe file from set1 and set2, find the intersection of these two sets, use it as an input of step 4, the other input of step 4 is a dummy input.

Total 410 probes discarded.

Case4:

Find average of each chip in set-two experiment (4,5,6 micrograms) For each probe in set two, calculate its correlation coefficient (CC) with the average of each chip in set two.

If CC<=0.5 discard this probe

Get discarded probe file, use it as an input of step 4. The other input of step 4 is a dummy input.

Total 4896 probes discarded in one embodiment.
concentration_correlation.pl

```
concentration_correlation.pl
Input:
1.ave_of_each_concentration
format: concentration average_of_gene_expression
2.discard_threshold (0–1, use 0.5 in one case)
Output:
Discard_probes_coeff_le_threshold
Format:
Gene_name    probe_coordinate_x    probe_coordinate_y
correlation_coefficient
```

Use this as an input of step 4

Step 4. Normalize probe intensities from different hybridizations globally at 130. (i.e. normalized by average of gene expressions in the chip).
normalization_pl

```
normalization.pl
input:
1.concentration_insensitive_probes_file1
2.concentration_insensitive_probes_file2
input_file_format (from step 3)
format:
Gene_name   probe_coordinate_x   probe_coordinate_y
space or correlation_coefficient
output:
image_file_name.norm_by_ave_of_all_blocks
format:
B_gene_number total_probes_for_this_gene gene_name
Probe_coordinate_x Probe_coordinate_y   normalized_intensity
```

Step 5. calculate the average($S_i$) and standard deviation ($SD_i$) for the hybridization signals observed on each oligo at 140.

Step 6. calculate the correction coefficient($C_i$) for each oligo by requiring its signal average equals to a constant (i.e. 1) at 150.

$$C_i = 1/S_i$$

Step 7. calculate the uncertainty coefficient at 160 for each oligo as the ratio between standard deviation and average $$d_i = SD_i/S_i$$

Running cal_coeff.pl does step 5,6,7
input is the output of step 4

```
Output:
Result_coeff
FORMAT:
B_gene_number   total_probes_for_this_gene gene_name
probe_coordinate_x y correction_coefficient_for_this_probe
probe_uncertainty
probe_standard_deviation
```

(5 columns)
negative value(correct coefficient)means this probe is a bad probe.

Use of Correction Coefficients:

Step 8. Discard the probe with high uncertainty at 170 (user determined, 0.5 is recommended). This may also be done as part of obtaining the correction coefficients in further embodiments. Calculate the corrected intensity for each probe at 210

$$S_i^{cor} = S_i * C_i$$

Step 9. Calculate a weighting factor at 220 and expression level at 230 for each probe. A weighted gene expression($V_i$) is determined:

$$w_i = \frac{1 - \alpha^{d_i S_i^{cor} / \Sigma d_i S_i^{cor}}}{\Sigma(1 - \alpha^{d_i S_i^{cor} / \Sigma d_i S_i^{cor}})}$$

$$V_i = \sum_{i=1}^{m} w_i s_i^{cor}$$

or calculate arithmetic mean without using the minimum and maximum values in the probe set. m is the number of used probes for this gene.

Step 10. Uncertainty of the gene expression level D is calculated 240:

$$D = 1/m \sum_{i=1}^{m} d_i S_i^{cor}$$

Step 11. Determine the absolute call for the gene at 250:
1. Background correction
    1.1. divides the chip to 16 regions
    1.2. take the average of lowest 2% of cell intensity values in this region. This is the background of this region, Subtract the background from the average intensities of all probes in this region.
2. Normalize probe intensities globally.
3. Apply the correction coefficient to each probe
4. Determine absolute call for the gene
    For each gene, find all used probes. Compare the intensity of each probe with 0.8, then a rank based Z-score is calculated for this gene
    A: absent −1 M: Marginal 0 P: present 1

```
if (z >= 0.5){
        call=1;
}
else if (z >= 0){
    if (norm_ave >= 0.8){
        call=1;
    }
    else{
        call = 0;
    }
}
else if (z > -1.5){
    if (norm_ave <= 0.5){
        call=-1;
    }
    else{
        call = 0;
    }
}
else{
    call=-1;
}
```

Steps 8-11, are done in one embodiment by running script "rank" or "rank_weight" (a c++ program. the source files are: block.cpp, block.h, main.cpp).

"rank" calculates arithmetic average for gene expression value input: image_name (a file containing image file names) correction_coefficient-file alpha(threshold for uncertainty, 0.5 recommended)

"rank_weight" calculate weighted average for gene expression input: image_name(a file containing image file names) correction_coefficient_file alpha(2.55 recommended)

Output:
1image_file_name_orgexp: a tab delimited file with 3 columns: gene_number gene_name gene_expression(before applying correction coefficient)
2. image_file_name_corexp: a tab delimited file with 4 columns: gene_number gene_name gene_expression(after applying correction coefficient) call for this gene
3. image_file_name.correct_intensity:a tab delimited files. Each gene begins with
B_gene_number gene_name total_probes used_probes(4 columns)
probe_coordinate_x y corrected_intensity_for_this_probe (3 columns)
4. image_file_name.gene_exp_uncertainty: a tab delimited file with 7 columns:

```
gene_name
corrected_expression
uncertainty
call
total_probes_for_the_gene
used_probes
Z_score
```

5. image_file_name.ave_all: average and standard deviation of gene expressions in the chip Calculation of Z-score and Call In one embodiment the Z-score and call can be calculated as follows. For each gene get: C as the corrected probe intensity and J as the total number of probes used. For each gene the used probes are the subset of probes on the chip or array that were determined to provide valid information about that gene. For example, for arrays having 16 probes representing a each gene, not all 16 probes may provide useful hybridization response, for example as a result of incorrect sequence or undesired cross-hybridization. Then for each gene:

1. Take the absolute difference |C−0.8| for each probe;
2. Omit from consideration those cases where |C−0.8|=0;
3. Rank the remaining absolute differences, from smallest to largest, employing tied ranks where appropriate;
4. Assign to each such rank a "+" sign when C−0.8>0 and a "−" sign when C−0.8<0;
5. Calculate S: sum of the rank, if S>0, S=S−0.5 else S=S+0.5;
6. Calculate variance V: $V=sqrt(J*(J+1)*(2*J+1)/6)$;
7. Calculate a Z-score: $Z=S/V$, Z score can then be converted to statistical P value by using a normal distribution form; and
8. Assign a user-defined threshold value for Z and calculate a call for each gene, where an appropriate call for this gene (Present, Marginal, Absent) can be made based on the threshold set by user. If call=1 then transcript is present in the sample, if call=0 then transcript is marginally present, and if call=−1 then transcript is absent. In the pseudocode above, the example threshold Z was set at 0.5.

The superiority of this method is based in part on the use of a value for each individual usable probe for a gene rather than a single averaged value of all probes for that gene.

Comparison of Different Call Methods:
1. Compare gene expression with its standard deviation
2. Compare gene expression with average, median, 25percentile and 75percentile of negative controls
3. Compare gene expression with its uncertainty
4. rank-based test, compare each probe with normalized, scaled expression in gDNA chip(ideally, it is 1, use 0.8 actually)
5. rank-based test as 4, also consider the average of gene expression(see step 11)

Performance test:
  1. wrong calls (A-P, A-M, M-P, specially A-P wrong call) in replica chips
  2. call for negative and positive controls in 39 rice chips
  3. call for panicle specific gene OS006283, root specific gene OS000876 in 39 rice chips The rank based method performs best, especially method 5. This is implemented in both "rank" and "rank_weight"

Comparison of Different Correction Coefficients:
1. result_coeff__0.14__0.34_intersect (from step 3 case 1)
2. result_coeff__0.17__0.07_union (from step 3 case 2)
3. result_coeff__0.17__0.07_intersect(from step 3 case 3)
4. result_coeff_concen_corr(from step 3 case 4)
5. result_coeff_no_conc__9_chip(without considering concentration insensitive probes, use 4, 5 6 microgram chips, each has 3 replicas, total 9 chips)

Performance Test:
1. wrong calls (A-P, A-M, M-P, specially A-P wrong call) in replica chips
2. call for negative and positive controls in 39 rice chips
3. call for panicle specific gene OS006283, root specific gene OS000876 in 39 rice chips Using rank-based method (i.e. call method 5)

In general, "result_coeff_no_conc__9_chip" correction coefficient is the best performer.
result_coeff__0.14__0.34_intersect performs slightly worse.

Recommendation:
Use "result_coeff_no_conc__9_chip" as correction coefficient
"rank" and "rank_weight" perform similarly, but "rank_weight" makes a little more M-P wrong calls than "rank".
Usage:
Running: rank file_containing_image_file_names result_coeff_no_conc__9_chip 0.5
Or: rank_weight file_containing_image_file_names result_coeff_no_conc__9_chip 2.55

Figure 3:
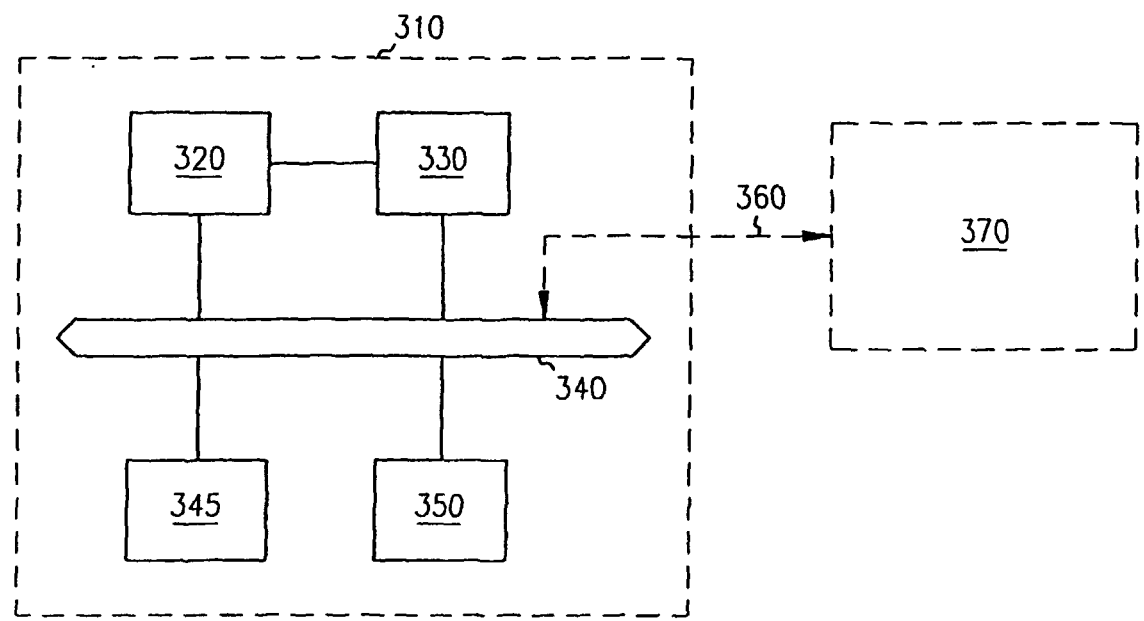
FIG. 3 is a block representation illustrating an exemplary embodiment of a system that generates and uses coefficients for oligo probes.

One embodiment for executing a computer program for generating and use coefficients for correction of oligo probes is illustrated in FIG. 3. A computer system 310 comprises a personal computer or other computer capable of executing computer programs. FIG. 3 is a simplified representation of the computer system 310 comprising a processor 320, a memory 330 and bus 340. The computer system further comprises circuitry and programming for input devices 345 and output devices 350. Input devices 345 comprise disk drives, keyboards, touchpads, and other devices for providing information to the processor 320 and memory 330. Output devices 350 comprise printers, displays, and other output connections.

In one embodiment, computer system 310 comprises a communications link 360 that is coupled to a network. A database server 370 is one device that is also coupled to the network, and hence to the computer system 310 via link 360. The computer system queries the database and receives results from the database. In some embodiments, the communication link is a local or wide area network. In further embodiments, the database server functions are provided by processor 320 utilizing input/output devices 345/350 such as a disk drive.

Although illustrated as connected via the bus 340, the components of the system 310 may be connected directly to each other in addition to, or instead of, being connected via the bus 340. Other conventional methods of communicating between components (e.g., conventional wireless communications means) may also be employed. Furthermore, various levels of integration between components may also be contemplated by the present invention. For example, any component may be integrated in part or in whole with any other component or components.

The invention will be further described by reference to the following detailed examples. These examples are provided for purposes of illustration only, and are not intended to be limiting unless otherwise specified.

EXAMPLES

Example 1

GENECHIP®Standard Protocol

A rice gene array and probes derived from rice RNA extracted from different tissues and developmental stages can be used to identify the expression profile of genes on the chip.

The standard protocol for using the GENECHIP® to quantitatively measure plant gene expression is carried out as outlined below:

Quantitation of Total RNA
  1. Total RNA from plant tissue is extracted and quantified using GeneQuant (Amersham Biosciences, Piscataway, N.J.)
     $1OD_{260}=40$ mg RNA/ml; $A_{260}/A_{280}=1.9$ to about 2.1
  2. Run gel to check the integrity and purity of the extracted RNA Synthesis of Double-stranded cDNA Gibco/BRL SuperScript Choice System for cDNA Synthesis (Cat #1B090-019) is employed to prepare cDNAs. T7-(dT)$_{24}$ oligonucleotides are prepared and purified by HPLC. (5'-

SEQ ID NO: 662)
(5'-GGCCAGTGAATTGTAATACGACTCACTATAGGGAGGCGG-
(dT)$_{24}$-3';.

Step 1. Primer hybridization:
Incubate at 70° C. for 10 minutes
Spin quickly and put on ice briefly
Step 2. Temperature adjustment:
Incubate at 42° C. for 2 minutes
Step 3. First strand synthesis carried out using:
DEPC—water—1:1
RNA (10: g final)—10:1
T7=(dT)$_{24}$ Primer (100 pmol final)—1:1 pmol
5×1$^{st}$ strand cDNA buffer—4:1
0.1M DTT (10 mM final)—2:1
10 mM dNTP mix (500:M final)—1:1
Superscript II RT 200 U/:1—1:1
Total of 20:1
Mix well
Incubate at 42° C. for 1 hour
Step 4. Second strand synthesis:
Place reactions on ice, quick spin
    DEPC—water—91:1
    5×2$^{nd}$ strand cDNA buffer—30:1
    10 mM dNTP mix (250 mM final)—3:1
    E. coli DNA ligase (10 U/:1)—1:1
    E. coli DNA polymerase 1-10 U/:1-4:1
    RnaseH 2U/:1—1:1
    T4 DNA polymerase 5 U/:1—2:1
    0.5 M EDTA (0.5 M final)—10:1
    Total 162:1
Mix/spin down/incubate 16° C. for 2 hours
Step 5. Completing the reaction:
Incubate at 16° C. for 5 minutes Purification of Double Stranded cDNA
1. Centrifuge PLG (Phase Lock Gel, Eppendorf 5 Prime Inc., pI-188233) at 14,000×, transfered 162:1 of cDNA to PLG
2. Add 162:1 of Phenol:Chloroform:Isoamyl alcohol (pH 8.0), centrifuge 2 minutes
3. Transfer the supernatant to a fresh 1.5 ml tube, add
    Glycogen (5 mg/ml) 2
    0.5 M NH$_4$OAC (0.75×Vol) 120
    ETOH (2.5×Vol, −20° C.) 400
4. Mix well and centrifuge at 14,000× for 20 minutes
5. Remove supernatant, added 0.5 ml 80% EtOH (−20° C.)
6. Centrifuge for 5 minutes, air dry or by speed vac for 5-10 minutes
7. Added 44:1 DEPC H$_2$O Analyze quantity and size distribution of cDNA
Run a gel using 1:1 ratio of the double-stranded synthesis product to loading buffer Synthesis of Biotinylated cRNA
(Enzo BioArray High Yield RNA Transcript Labeling Kit Cat #900182)

| | |
|---|---|
| Purified cDNA | 22:1 |
| 10 × Hy buffer | 4:1 |
| 10 × biotin ribonucleotides | 4:1 |
| 10 × DTT | 4:1 |
| 10 × Rnase inhibitor mix | 4:1 |
| 20 × T7 RNA polymerase | 2:1 |
| Total | 40:1 |

Centrifuge 5 seconds, and incubate for 4 hours at 37° C. Gently mix every 30-45 minutes Purification and Quantification of cRNA

| (Qiagen Rneasy Mini kit Cat# 74103) | | |
|---|---|---|
| cRNA | 40:1 | |
| DEPC H$_2$O | 60:1 | |
| RLT buffer | 350:1 | mix by vortexing |
| EtOH | 250:1 | mix by pipetting |
| Total | 700:1 | |

Wait 1 minute or more for the RNA to stick
Centrifuge at 2000 rpm for 5 minutes
    RPE buffer 500:1
Centrifuge at 10,000 rpm for 1 minute
    RPE buffer 500:1
Centrifuge at 10,000 rpm for 1 minute
Centrifuge at 10,000 rpm for 1 minute to dry the column
    DEPC H$_2$O 30:1
Wait for 1 minute, then elute cRNA from by centrifugation, 10K 1 minute
    DEPC H$_2$O 30:1
Repeat previous step
Determine concentration and dilute to 1: g/:1 concentration Fragmentation of cRNA

| | |
|---|---|
| cRNA (1:g/:1) | 15:1 |
| 5 × Fragmentation Buffer* | 6:1 |
| DEPC H$_2$O | 9:1 |
| | 30:1 |

*5× Fragmentation Buffer

| | |
|---|---|
| 1M Tris (pH 8.1) | 4.0 ml |
| MgOAc | 0.64 g |
| KOAC | 0.98 g |
| DEPC H$_2$O | |
| Total | 20 ml |

Filter Sterilize

Array Washed and Stained In:
    Stringent Wash Buffer**
    Non-Stringent Wash Buffer***
    SAPE Stain****
    Antibody Stain*****

Washed on Fluidics Station Using the Appropriate Antibody Amplification Protocol

**Stringent Buffer: 12×MES 83.3 ml, 5 M NaCl 5.2 ml, 10% Tween 1.0 ml, $H_2O$ 910 ml, Filter Sterilize

***Non-Stringent Buffer: 20×SSPE 300 ml, 10% Tween 1.0 ml, $H_2O$ 698 ml, Filter Sterilize, Antifoam 1.0.

****SAPE stain: 2× Stain Buffer 600:1, BSA 48:1, SAPE 12:1, $H_2O$ 540:1.

*****Antibody Stain: 2× Stain Buffer 300:1, $H_2O$ 266.4:1, BSA 24:1, Goat IgG 6:1, Biotinylated Ab 3.6:1

Characterization of Gene Expression Profiles. In one embodiment a rice gene array and probes derived from rice RNA extracted from different tissues and developmental stages are used to identify the expression profile of genes on the chip. In the case of the rice array that contains over 23,000 genes (approximately 18,000 unique genes) or roughly 50% of the rice genome, and is similar to the *Arabidopsis* GeneChip® (Affymetrix) with the exception that the 16 oligonucleotide probe sets do not contain mismatch probe sets. The level of expression is therefore determined by internal software that analyzes the intensity level of the 16 probe sets for each gene. The highest and lowest probes are removed if they do not fit into a set of predefined statistical criteria and the remaining sets are averaged to give an expression value. The final expression values are normalized by software in the present application. The advantages of a gene chip coupled with the present method of normalization and calling are, quantitative results, a highly reproducible system, enabling a global gene expression analysis, and a higher sensitivity than Northern blot analyses.

Example 2

Application of the Present Invention for Global Transcriptome Remodeling During *Brassica* Seed Pre-Germination The present invention was applied to enable characterizing global transcriptional regulation during seed pre-germination. The initial steps of seed germination require global changes in the underlying biology of all the cells involved, before the embryo can begin the process of growth and emergence. Pre-germination treatments consisting of partial hydration of seeds are used to improve seed germination vigor. Here we investigate whether *Brassica* is sufficiently closely related to *Arabidopsis* to allow use of an *Arabidopsis* whole-genome microarray to investigate changes in gene expression. Such cross-species microarray hybridization is becoming a well-characterized and accepted technique (Zhu, T., Chang, H.-S., Schmeits, J., Gil, P., Shi, L., Budworth, P., Zou, G., Chen, X. and Wang, X. (2001). Gene Expression Microarrays: Improvements and Applications Towards Agricultural Gene Discovery. J. Assoc. Lab. Automation 6, 95-98; Zhu, T., Budworth, P., Han, B., Brown, D., Chang, H.-S., Zou, G. and Wang, X. (2001) Toward elucidating the global gene expression patterns of developing *Arabidopsis*: Parallel analysis of 8300 genes by a high-density oligonucleotide probe array. Plant Physiol. Biochem. 39, 221-242; Chismar, J. D., Mondala, T., Fox, H. S., Roberts, E., Langford, D., Masliah, E., Salomon, D. R. and Head, S. R. (2002) Analysis of result variability from high-density oligonucleotide arrays comparing same-species and cross-species hybridizations. Biotechniques 33, 516-524). The effect of the pre-germination treatments of partial hydration ('priming'), heating combined with partial, gradual dehydration ('shelf-life induction'), and full dehydration (by incubation at low relative humidity in a rotating drum without heating), are investigated using genomic scale microarray technology. An *Arabidopsis* whole-genome microarray (Affymetrix GeneChip®) was used to characterize responses of genomic transcription in *Brassica* seeds to initial hydration or priming, and subsequent heating and drying treatments used to prolong shelf life of dried seed.

*Brassica* seed was selected because its well-established seed treatment procedures, its close phylogenetic relationship to *Arabidopsis*, and the commercial value of *Brassica* species as crops make it a clear potential beneficiary of *Arabidopsis* functional genomics. Cauliflower (*Brassica oleracea* L. convar *botrytis* L. Alef. var. *botrytis*) is a vegetable crop where priming and shelf-life induction are well established, and applied on a commercial scale. Its relatively large seeds help to allow temperature and moisture content to be reproducibly controlled. Phylogenetic analyses based on DNA sequences have indicated the close relationship between the genera *Brassica* and *Arabidopsis*. Recent comparative genomic analyses have clearly demonstrated both synteny and microsynteny between *Arabidopsis* and *Brassica*, even though *Brassica oleracea* may lack homologs of some *Arabidopsis* genes.

Here, probes showing consistent hybridization between *Arabidopsis* and *Brassica* DNA were identified and used for the data analysis. Three global expression patterns were observed in the resulting expression profiles of treated *Brassica* seed. Of 17,886 detected transcripts, 7,731 were included in a cluster induced by hydration and repressed by gradual dehydration with heating, a response pattern characteristic of the components of protein synthesis and energy generation. Of 17,886 detected transcripts, 4,916 genes showed reduced expression in response to hydration. Many of these repressed transcripts were unaffected by gradual dehydration with heating, a response characteristic of seed storage protein messages.

The hybridization of the cauliflower genome to the *Arabidopsis* array with the methods described herein provided confidence that only the expression patterns of orthologous genes are described.

Experimental Procedures.

Seed germination treatments. Seeds of cauliflower varieties Lintop and Maverick were primed for 4 days followed by either shelf-life induction or by direct drying according to Bruggink (Bruggink, G. T., Ooms J. J. J. and van der Toorn, P. (1999). Induction of longevity in primed seeds. Seed Sci. Res. 9, 49-53). Priming consisted of elevating the seed moisture content to 54% (dry weight basis) and transferring seeds to a rotating drum (10 rpm), which was kept in the dark at 20° C. At the end of this period seeds were either directly dried by exposing them to moving air of 20 C and 40% RH for 24 hours, after which they were stored at 20° C. and 40% RH. Alternatively they were transferred to shelf-life induction conditions (Bruggink et al., 1999). These conditions consisted of a relative humidity of 100% and a temperature of 32° C. for 48 hours, followed by drying. Drying in this case consisted of linearly reducing temperature and relative humidity to 20° C. and 28% respectively. At the end of this period seeds were placed at 40% relative humidity and 20° C. for storage.

To test potential longevity dried seeds were equilibrated at 75% RH and 20° C. for 3 days and then divided over aluminum bags which were subsequently sealed and put in a hot water bath at 46° C. After periods of 0, 2, 3, 4, 5 and 6 days bags were removed from the water, opened and the seeds put to germinate on moistened filter paper, with two replicates of 100 seeds each. The percentage of seeds developing into a normal seedling was determined after 10 days at 20° C.

DNA and RNA extraction. Seeds before and after various treatments were excised and stored in RNA later buffer (Ambion). DNA was extracted using CsCl2 gradient centrifugation (Sambrook, J., Fritsch, E. F. and Maniatis, T. (1989). Molecular cloning: A laboratory manual. $2^{nd}$ ed. Cold Spring Harbor Press, Plainview, N.Y.). Total RNA was extracted with phenol-chloroform-isoamyl alcohol (25:24:1), precipitated with ethylene glycol monobutyl ether, and then re-suspended in water and further purified through LiCl precipitation (Sambrook et al., 1989). The RNA was further examined by gel electrophoresis for integrity and by spectrometry for purity. To ensure data quality, only samples with A260/A280 ratios of 1.9-2.1 were included in the study.

Microarray experiment and data acquisition. A total of 3 ug of genomic DNA was mixed with 20 ul of 2.5× random hexamers and heated at 100° C. for 5 minutes. The mixture was cooled on ice immediately and labeled with biotin-dNTPs at 37° C. for 2 hours in the presence of Klenow DNA fragment using BioPrime DNA labeling system (Invitrogen, Carlsbad, Calif.). The RNA labeling and hybridization were performed as previously described (Zhu, T., Chang, H.-S., Schmeits, J., Gil, P., Shi, L., Budworth, P., Zou, G., Chen, X. and Wang, X. (2001) Gene Expression Microarrays: Improvements and Applications Towards Agricultural Gene Discovery. J. Assoc. Lab. Automation 6, 95-98; Zhu, T., Budworth, P., Han, B., Brown, D., Chang, H.-S., Zou, G. and Wang, X. (2001) Toward elucidating the global gene expression patterns of developing *Arabidopsis*: Parallel analysis of 8300 genes by a high-density oligonucleotide probe array. Plant Physiol. Biochem. 39, 221-242). Briefly, Total RNA (5 µg) from each sample was reverse transcribed at 42° C. for 1 hr using 100 pmol of the oligo dT(24) primer containing a 5' T7 RNA polymerase promoter sequence, 50 mM Tris-HCl (pH 8.3), 75 mM KCl, 3mM MgCl2, 10 mM dithiothreitol (DTT), 0.5 mM dNTPs, and 200 units of SuperScript II reverse transcriptase (Life Technologies). The second strand of cDNA was synthesized using 40 units of *E. coli* DNA polymerase I, 10 units of *E. coli* DNA ligase and 2 units of R Nase H in a reaction containing 25 mM Tris-HCl (pH 7.5), 100 mM KCl, 5 mM MgCl2, 10 mM (NH4)SO4, 0.15 mM b-NAD+, 1 mM dNTPs, and 1.2 mM DTT. The reaction proceeded at 16° C. for 2 hours and was terminated using EDTA. Double-stranded cDNA products were purified by phenol/chloroform extraction and ethanol precipitation.

Biotinylated complementary RNAs (cRNAs) were transcribed in vitro from synthesized cDNA by T7 RNA Polymerase (ENZO BioArray High Yield RNA Transcript Labeling Kit, Enz6). cRNAs were purified using affinity resin (Qiagen RNeasy Spin Columns) and randomly fragmented by incubating at 94° C. for 35 minutes in a buffer containing 40 mM Tris-acetate (pH 8.1), 100 mM potassium acetate, and 30 mM magnesium acetate to produce molecules of approximately 35 to 200 bases. The labeled DNA and RNA samples were mixed with 0.1 mg.ml-1 sonicated herring sperm DNA in a hybridization buffer containing 100 mM 2-N-morpholino-ethane-sulfonic acid (MES), 1 M NaCl, 20 mM EDTA, 0.01% Tween 20, denatured at 99° C. for 5 min, and equilibrated at 45° C. for 5 min before hybridization. The hybridization mix was then transferred to the rice GENE-CHIP® microarray cartridge and hybridized at 45° C. for 16 hours on a rotisserie at 60 rpm.

The hybridized arrays were then rinsed and stained in a fluidics station (Affymetrix). They were first rinsed with wash buffer A (6×SSPE (0.9M NaCl, 0.06 M NaH2PO4, 0.006 M EDTA), 0.01% Tween 20, 0.005% Antifoam) at 25° C. for 10 min and incubated with wash bufferB (100 mM MES, 0.1 M NaCl, 0.01% Tween 20) at 50° C. for 20 min, then stained with Streptavidin Phycoerythrin (SAPE) (100 mM MES, 1M NaCl, 0.05% Tween 20, 10 mg/ml SAPE 2mg/ml BSA) at 25° C. for 10 min, washed with wash buffer A at 25° C. for 20 min and stained with biotinylated anti-streptavidin antibody at 25° C. for 10 min. After staining, arrays were stained with SAPE at 25° C. for 10 min and washed with wash buffer A at 30° C. for 30 min. The probe arrays were scanned twice, and the intensities were averaged with an Agilent GeneArray Scanner using GENECHIP® Suite 4.0 (Affymetrix).

Microarray data processing and analysis. The .DAT files of raw images generated by the scan of the microarray were used to generate .CEL files with Affymetrix MAS 4.0. The .CEL files generated in this manner, containing the signals of each oligonucleotide probe feature, were then analyzed using a custom scripts written in PERL 5.6. The .CEL files generated by genomic DNA hybridization were compared at the individual probe level in order to generate a database of probes hybridizing to the *Brassica* genome with 75% or less of the signal than the *Arabidopsis* genome. The perfect match probe values from the microarrays hybridized to *Brassica* RNA were then compared to the database; 'bad' probes were removed from the analysis, and then the $72^{nd}$ percentile value of the remaining probes was calculated. These raw signal values were then corrected by subtracting a background estimate obtained from the $5^{th}$ percentile of the signal values, and scaled to a target mean of 100. Before data analysis, the values were normalized by median centering to a target of 1 on a per-gene basis. Self-organizing maps were generated using GeneSpring 4.2 (Silicon Genetics), which was also used to generate several of the figures.

Removal of hybridization data for non-hybridizing oligonucleotide probes increases data quality and simplifies interpretation. Most of the experiments described in this example were conducted using a custom designed oligonucleotide microarray containing 382,166 oligonucleotide probes of 25 base pairs each. These sequences were designed to perfectly match 25, 996 unique *Arabidopsis* genes (representing over 99% of the predicted exons in the *Arabidopsis* genome at the time of design). Consequently each gene is represented by a probe set of, on average, 15 oligonucleotide probes. The probe set hybridization data, of 15 intensity values on average for each gene ID, is used to calculate the expression value for that gene, which is taken as the $72^{nd}$ percentile of the normalized probe cell intensity values for each probe set.

The utility of the *Arabidopsis* array for *Brassica* gene expression analysis was determined by estimating the rate of nucleotide substitution between *Brassica oleracea* and *Arabidopsis thaliana*. Three full-length *Brassica* coding sequences with clear *Arabidopsis* orthologs were compared using pairwise Martinez/Needleman-Wunsch alignment (Chlorphyllase I, *Arabidopsis*=At1g19670, *Brassica*=GB: AF337544; Ethylene receptor ETR2, A.=At3g23150, B.=EMBL: AB078598; 40s ribosomal protein, A.=At3g02560, B. =EMBL: AF144752). The nucleotide substitution rates between these sequences were 20.5%, 19.7% and 20%, respectively.

Assuming the median of these measurements is close to that for all genes (20% substitution rate or 80% sequence identity), the probability of any 25 base-pair probe being 100% identical to *Brassica* can be estimated at $0.8^{25}$, so 99.62% of probes will be expected to contain a mismatch. Despite this, 75% of the probes on an array hybridized to *Brassica* DNA were found to be within 50% of the signal intensity of the identical probes hybridized to *Arabidopsis* DNA. It was found that probes with 12 bp or more of identical sequence, depending on factors such as GC content and secondary structures, were capable of producing hybridization signals indistinguishable between *Brassica* and *Arabidopsis* (data not shown). Using the estimate of substitution rate above, 68.7% of probes would be expected to have 12 or more contiguous identical bases.

The cell intensity values for each oligonucleotide probe in two replicated arrays hybridized to *Arabidopsis* ecotype Columbia genomic DNA were compared. 91.5% of probes in the first replicate *Arabidopsis* array had at least 50% of the signal intensity of the probes on the second array. The comparison of *Brassica* and *Arabidopsis* genomic DNA hybridized arrays was then used to define a list of useful probes, which hybridize to *Brassica* genomic DNA with at least 75% of the intensity of *Arabidopsis* DNA. Since the arrays contain several redundant probes for each gene, it is possible to remove a substantial number of probes from the analysis and still to obtain a robust result. Consequently, all the probes where *Brassica* genomic hybridization was less than 75% of the signal from *Arabidopsis* (143,361 probes, or 37.5%) were designated "unusable"; we have high confidence that the remaining 62.5% of probes are recognizing orthologous or related sequences in *Brassica* to the *Arabidopsis* gene to which the probes were designed. Only the probes in each probe set where *Brassica* genomic DNA hybridized with at least 75% of the signal from *Arabidopsis* (9 per gene on average), were used in the expression analysis algorithm.

The advantage of using only the probes designated "usable" on the correlation of expression values from control genomic DNA hybridization is demnstatred using a fourth microarray also hybridized to *Brassica* genomic DNA. Although the average probe number per probe set was reduced from 15 to 9 after removal of the unusable probes, the correlation coefficient between *Brassica* and *Arabidopsis* genomic hybridization improved from 0.69 of unmodified analysis to 0.75 by the use of only the usable "homologous" probes. This superiority of the present method is clearly seen by using scatter plots of all signal values derived from *Arabidopsis* and *Brassica* genomic DNA hybridization to the *Arabidopsis* microarray for the usual standard analysis (all probes) and the analysis excluding 'bad' probes ("usable probes"). The scatter plots indicate the reproducibility of replicate hybridizations to mRNA samples. These data support the assumption that the expression values we infer from our analysis of microarrays hybridized to *Brassica* MRNA are likely to represent measurements of the expression level of genes with high nucleotide-level identity to those in *Arabidopsis*. We compared the reproducibility of RNA detection by comparing the same *Brassica* RNA sample hybridized to two microarrays, analyzing both arrays with both algorithms, and comparing the correlation between replicates for each algorithm. The correlation in both cases was very high (0.99) with no loss of reproducibility by exclusion of probes. Consequently we do not expect (and have not observed) the use of a restricted probe set to strongly affect the relative expression values between *Brassica* RNA samples.

The Expression of The 17,886 Genes Detected Creates Three Distinct Pre-Germination Patterns. Using this superior method, reliable conclusions were made concerning how pre-germination treatments affect seed germination rate and longevity and the pattern of genes expressed under those conitions. RNA used for analysis was extracted from *Brassica* seeds, which were either untreated or subjected to four successive treatments corresponding to established procedures designed to optimize germination rates. In the analyses untreated seed, seed treated by partial hydration to 54% moisture or "priming," seeds dried to 6% moisture (priming followed by drying), and seeds treated by priming but instead of drying, exposed to the partial dehydration with heating referred to as shelf-life induction (Bruggink, G. T., Ooms J. J. J. and van der Toom, P. (1999) Induction of longevity in primed seeds. Seed Sci. Res. 9, 49-53, Materials and Methods)). Subsequently RNA for seeds partially hydrated, partially dried with heating (shelf life induced) and then dried fully) were harvested.

These seed treatments delivered the expected effects on germination efficiency and longevity in both cultivars. The effects of the partial hydration or priming treatment, and the priming treatment followed by a partial dehydration (shelf life induction) treatment with heating, on time taken to germination were determined. In all cases treated seed germinated faster than untreated. The induction treatment after priming led to a slightly larger increase in rapidity than priming alone.

It was observed that viability of untreated seeds is reduced to half its original value after 4 to 6 days in both cultivars. For primed seeds this reduction is reached after around 2 days. Seeds partially dried with heating (shelflife induction) after priming showed similar longevity to untreated seeds. In summary, primed seed germinated more rapidly but deteriorated more quickly, and this was reversed by the shelf life treatment of gradual dehydration with heating.

Gene Expression. The microarray data was analyzed using the algorithm described herein, where probes hybridizing to *Brassica* DNA with less than 75% of the signal of *Arabidopsis* DNA were excluded from the signal (gene expression value) calculations. The data were then filtered to remove low-level random values by exclusion of transcripts below the detection threshold. Based on the coefficient of variation of the negative control probes, a signal value of 25 was considered to represent the threshold of detectability. Any gene where no two replicate data points of the ten microarrays used reached a signal of 25 was excluded from the analysis (all genes where all the probes were eliminated were also removed from the analysis at this step). Among 26,367 genes with *Arabidopsis* probe sets, 17,886 genes met our preliminary filter criteria; the remaining genes we conclude are either not expressed in *Brassica* seed at high enough levels to detect with confidence, or are substantially polymorphic between *Arabidopsis* and *Brassica*. The expression profiles of all of these genes, with values normalized to the median on a per-gene basis, are shown in FIG. 3A for the five treatment points described. Values represent the mean of the signal values from two independent replicate microarray experiments.

It was found that three distinct expression patterns were clearly visible among these genes with detectable mRNA levels in seed. Clustering the median-centered data using self-organizing maps effectively separated these three major patterns. The first, and largest, group of 7,731 transcripts are induced by the 'hydration' step, relatively unchanged by the drying step, repressed by the 'gradual dehydration' (shelf life induction) step and again relatively unchanged by drying. This behavior is consistent with genes that are involved in the mediation of seed responses to hydration, and whose response to priming is reversed by the gradual dehydration/induction treatment. Since this group represents 43% of all the genes detected in seed, the response to seed hydration clearly occurs on a genomic scale. Compared with other studies which have, for example, shown that 10% of investigated transcripts respond strongly to light in etiolated seedlings (Tepperman, J. M., Zhu, T., Chang, H. S., Wang, X. and Quail, P. H. (2001) Multiple transcription-factor genes are early targets of phytochrome A signaling. Proc Natl Acad Sci USA. 98, 9437-9442) this result emphasizes the global nature of the changes in the seed or seedling genome during early developmental transitions such as germination and de-etiolation.

The MIPS classification system (http://mips.gsf.de/proj/thal/) was used to determine which functional classes of proteins are encoded by the transcripts in each of the three expression pattern clusters. This system has the advantage that it provides a putative functional category for most genes in the *Arabidopsis* genome. A functional category was assigned to all of the detected transcripts. Note that the detected transcripts closely mirror the overall proportion of the genome with the exception of a reduction in the percentage of unknowns (probably many of these genes are mis-annotated or expressed at low levels) and an increase in the proportion of metabolic genes (a well characterized and highly expressed group). The relative abundance of each functional category in each of the co-regulated groups was also determined. The cluster of genes that are up-regulated by the hydration treatment (cluster 1) are enriched in proteins involved in translation and protein synthesis (361 of the detected transcripts fell into this category, 253 of them in cluster 1; significant by chi-squared at $P=2.5\times10^{-25}$). Proteins involved in energy production and protein degradation and folding were also over-represented in this cluster (372 of 752 degradation and folding, $P=5.4\times10^{-4}$; 118 of 246 energy, $P>0.05$). These observations are consistent with previous results at the single-protein or activity level that protease activities (Muntz, K. (1996) Proteases and proteolytic cleavage of storage proteins in developing and germinating dicotyledonous seeds. J. Exp. Bot. 47, 605-622) and protein synthesis (Bray, C. M. (1995). Biochemical processes during the osmopriming of seeds. In: Kiegel, J. and Galili, G. (eds). Seed development and germination. $1^{st}$ edition, pp 767-789. Marcel Dekker, New York; Bewley, J. D. and Marcus, A. (1990) Gene expression in seed development and germination. Prog. Nucleic Acid Res. Mol. Biol. 38, 165-193) are activated when seeds are hydrated, but demonstrate that a global effect is seen on genes in these classes.

The 5239 genes in cluster 2 are mostly unaffected by the hydration and dehydration steps. The transcripts in this group are consequently of less direct relevance to the mechanism of action of pre-germination treatment. Nonetheless, this group is deficient in protein synthesis components and has a higher-than-expected proportion of genes involved in ionic homeostasis, and transposon transcripts (which is consistent with a lack of known roles for these transcripts in seed germination). The presence of this cluster is informative, however, as it shows that the transcription of some genes is not affected by the hydration of seeds, and thus that the response of gene expression is regulated in a gene- or region-specific manner, rather than being a result of a functionally blind, global alteration in expression patterns.

The third cluster including 4916 genes shows no strong enrichment in any of the general MIPS functional categories, although the general MIPS categories do not separate storage proteins. This group contains somewhat fewer protein synthesis components and more plant-specific proteins (not significant) than the previous two. This cluster has almost the inverse response pattern of the first, in that most of the genes are strongly repressed by the hydration treatment. However, any of the genes repressed by hydration in this group are not reversed by a subsequent induction in response to gradual dehydration. Many genes change in this cluster change only slightly, but several transcripts are strongly hydration-repressed, by more than an order of magnitude in some cases.

The expression of all *Brassica* genes showing a detectable hybridization signal to an *Arabidopsis* array was characterized. We defined as detectable 75% of the signal from *Brassica* DNA of that obtained with *Arabidopsis* DNA hybridized to a 25 bp oligonucleotide under conditions whose stringency should allow only a strongly similar sequence match to bind. Therefore, that the genes characterized here in *Brassica* correspond closely at the nucleotide homology level to their orthologs in *Arabidopsis*. The expression analysis of *Brassica* using oligonucleotide microarrays designed based on the *Arabidopsis* genome coupled with the method of the present invention, is a valid and valuable tool for the analysis of gene expression in cruciferous species.

The genomic scale of the responses to seed initial hydration are indicated by the result that 12,647 of 17,886 detected transcripts respond to initial hydration by an increase or decrease of expression level. This vast change in the allocation of resources across the genome probably reflects a complete shift in the metabolism of every cell in the seed. The genome-scale alteration in transcriptional activity is independent of the cultivar or measurement technology used. The sheer extent of de novo mRNA (and presumably protein) synthesis indicates that it is the genome that appears to be controlling the early process of germination, rather than germination proceeding with required components that pre-exist in the cell. We conclude that the major factor affecting seed longevity is probably the extent to which the energy-intensive pathways of protein synthesis and respiration are induced. Gradual dehydration is an effective way to repress the expression of the genes in these pathways to levels found in untreated seed. However, induction of these pathways is not required in order for the seeds to display increased germination efficiency. One factor, which may affect germination efficiency substantially, is the abundance of storage protein messages. This easily measured quantity may be used to characterize the quality and efficacy of pre-germination treatments applied to commercial seeds.

Example 3

Contribution of Transcriptional Regulation to Natural Variations in *Arabidopsis*

Genetic control of transcription and translation of genes are key components in genome evolution. To understand the transcriptional basis of natural variation among *Arabidopsis* accessions, in this example is presented a study of genome-wide variations in gene expression. MRNA levels of 8300 genes in different organs under the same growth conditions were monitored among five accessions: Col-0, C24, Ler, WS-2, and NO-0. The comparability of gene expression among accessions was established based on comparative genomic hybridization to the GENECHIP® microarray where probe sets sharing common sequences to target DNA of different accessions were selected. 6573 probe sets with no substantial genomic sequence variations among the accessions were identified and used for accession-specific gene expression analysis. Correlation analysis of expression patterns of these genes between pairs of accessions identified a group of 93 highly plastic genes with distinct expression patterns in each accession, suggesting the existence of variations in the regulatory mechanisms for these genes among different accessions. In contrast to those genes with high polymorphism in the coding regions identified by genomic hybridization, which include genes encoding transposon-related proteins, kinases, and disease-resistance proteins, genes in this 93 gene group included those with functions in transcription, environment sensing, stress response, and primary metabolism, suggesting that genes involved in these processes may contain nucleotide polymorphisms in their regulatory elements which could possibly be the primary targets of natural selection during *Arabidopsis* evolution. Only limited studies have attempted to correlate molecular studies of genotype with those of phenotypes (Streelman, J. T., and Kocher, T. D. (2000). From phenotype to genotype. Evol. Dev. 2, 166-173).

The objective of this study was to identify differences in gene expression among different *Arabidopsis* accessions, and in combination with genetic data, to understand the regulatory mechanism responsible for the gene expression differences. *Arabidopsis* was selected for such studies because of the large collections of geographically distinct populations with known genetic and phenotypic variations; available genome information, including both regulatory and coding sequences (*Arabidopsis* Genome Initiative 2000); and available functional genomic tools such as GENECHIP® microarray (Zhu, T., and Wang, X. (2000) Large-scale profiling of the *Arabidopsis* transcriptome. Plant Physiol. 124, 1472-1476). In this example is reported the transciprtome variations in five *Arabidopsis* accessions, detected by the *Arabidopsis* GENE-CHIP® microarray, and their implications in regulatory evolution.

Materials and Methods.

Plant Materials, Growth Conditions, and Sample Processing. Seeds form five *Arabidopsis* accessions, Col-0, C24, WS-2, NO-0, and Ler, were obtained from the *Arabidopsis* stock center (ABRC, Columbus, Ohio). All plants were grown in a conviron at 22° C. under a 12:12 light/dark cycle. RNA was extracted from various organs, including roots, leaves, flowers, and siliques, which were collected at different ages of plants. Genomic DNA was extracted mainly from the leaves. DNAse I digestion was used to obtain genomic DNA fragments with average sizes ranging from 25 nt to 150 nt. DNA fragments were end-labeled using terminal transferase according to Winzeler et al. (Winzeler, E. A., Richards, D. R., Conway, A. R., Goldstein, A. L., Kalman, S., McCullough, M. J., McCusker, J. H., Stevens, D. A., Wodicka, L., Lockhart, D. J., and Davis, R. W. (1998). Direct allelic variation scanning of the yeast genome. Science 281, 1194-1197). The RNA extraction and GENECHIP® microarray experiments were performed as described by Zhu et al. (Zhu, T., Budworth, P., Han, B., Brown, D., Chang, H. S., Zou, G., and Wang, X. (2001) Toward elucidating the global gene expression patterns of developing *Arabidopsis*: Parallel analysis of 8300 genes by high-density oligonucleotide probe array. Plant Physiol. Biochem. 39, 221-242).

Dataset Collection, Data Processing, and Data Analyses. The microarray experiments of genomic DNA hybridization were conducted in duplicates only for Col-0 and Ler, and not for the other three accessions. The microarray data from genomic DNA hybridization were processed according to the following procedure. First, any average difference in signals that was less than 5 was adjusted to 5. According to Affymetrix, Inc., the average difference is defined as the sum of differences between the signal obtained from perfect match probes and mismatch probes, divided by the total number of probe pairs. Then, genes that were called "absent" or "marginal" in either one of the five accessions were eliminated from the analysis. The outlier genes from the Col-0 and Ler replicates (false positives) were also eliminated. The outliers were defined as those genes that were called "present" in both replicates, whose average differences were greater than or equal to 25, and which were at least 2-fold different between the two replicates. For the rest of the genes, the average was taken from the two replicates and was used in the normalization of mRNA expression data.

Genes for the correlation analysis were selected from the gene list processed from genomic DNA hybridization data. Then, genes whose expression could not be detected (called "absent" or "marginal" and having average differences less than 25) across all the RNA samples from at least one accession were further eliminated. These genes include ones whose genomic DNA was present but whose expression could not be detected in any of the RNA samples. Excluded were these genes to avoid their interference with the correlation analysis, since there is no variation among all the samples (the expression values were all equal to 5 after flooring). The expression values of the selected genes were normalized to the corresponding genomic DNA by dividing the average differences from RNA hybridization by the average differences from genomic hybridization. The normalized values were the $\log_2$-transformed (log base 2) and used for the correlation analysis. In addition, this original dataset was used for permutations in which for a particular organ, at a particular developmental stage, we randomly permutated the five RNA samples from the five accessions, thus preserving the organ, age categorization. Then, for each gene, 10 pair-wise comparisons were made from the 5 different accessions and the Pearson Correlation Coefficients were calculated. The number of genes that had r<0.5 in a given pair of compared accessions was calculated. With the permutated data, the average of the 10 permutated datasets were calculated.

Cluster analysis of mRNA expression data was performed with the same list of genes used for the correlation analysis. The expression values of the selected genes were normalized to the corresponding genomic DNA by dividing the average differences from RNA hybridization by the average differences from genomic hybridization. The normalized expression values were then $\log_2$-transformed, mean centered for each gene across all the samples, and subjected to the self-organizing maps, followed by complete linkage hierarchical clustering of both genes and experiments using Cluster and visualized with Treeview.

Validation of the GENECHIP® microarray data. The genomic sequence for gene 13903_at (At3g54050) and 17392_s_at (At3g53260) from accession C24 was obtained by polymerase chain reaction (PCR) with genomic DNA from C24, and primers based on the gene's coding sequence from Col-0 were used. The PCR product was then sequenced and these sequences were used for designing gene specific primers and probes for Taqman assay. The Ler sequences of genes 12222_s_at (At2g20990), 14097_at (At2g47770), 20561_at (At2g46930), 14634_s_at (At4g27440), 13483_at (At2g25650), 15290_at (At2g20840), 13111_at (At2g38040), 14072_at (At1g67480), 14172_at (At3g54140), 14947_at (At4g37450), 16892_at (At5g45890), 17860at (At4g27410), 20545_at (At5g27470) were obtained by blasting the full-length cDNA sequences or CDS of these genes from Col-0 against the Ler sequences available from TIGR (ftp.tigr.org/pub/data/a thaliana/Ler). Top blast hits were chosen and sequences common for both Col-0 and Ler and used for designing gene specific primers and probes for Taqman assay. Quantitative RT-PCR (Taqman) assays were performed on an ABI PRISM® 7700 (Applied Biosystems, Foster City, Calif.), as previously described using gene specific primers and probe sets. A standard curve consisting of serial 1:5 dilutions was prepared with RNA concentrations of 50 ng/µl, 10 ng/µl, 2 ng/µl, 0.4 ng/µl, and 0.08 ng/µl. Relative expression levels were interpolated by comparison with standard curves with a correlation coefficient of 0.99 or greater. Relative expression levels were normalized to the expression level of the *Arabidopsis* APX3 gene, which was expressed at a constant level. All reactions were performed in triplicate.

Results

Establishment of Comparability of Gene Expression among Accessions. To compare gene expression among different accessions, probe sets with no substantial sequence variation among the five accessions, Col-0, C24, Ler, WS-2 and NO-0 were selected by genomic DNA hybridization. Genomic DNAs from different accessions were fragmented, labeled, and hybridized to the *Arabidopsis* GENECHIP® microarrays (Winzeler, E. A., Richards, D. R., Conway, A. R., Goldstein, A. L., Kalman, S., McCullough, M. J., McCusker, J. H., Stevens, D. A., Wodicka, L., Lockhart, D. J., and Davis, R. W. (1998) Direct allelic variation scanning of the yeast genome. Science 281, 1194-1197). The hybridization signals at the probe-set level were used as an indication of sequence similarity between the oligonucleotide probe sets (the probe sets were mostly from Col-0 (Zhu, T., and Wang, X. (2000) Large-scale profiling of the *Arabidopsis* transcriptome. Plant Physiol. 124, 1472-1476) and the target genomic DNA from the accessions being studied. The substantial differences in the probe set sequences of different accessions were determined based on the absolute "call", a parameter that measures the percentage of positive probe pairs across the probe set. Consistently detectable signals from a probe set (that is, a "present" call) of one gene mean that there are no substantial differences between the oligonucleotide probe set sequences and the examined target genomic DNA, and consistently low signals (an "absent" call) suggest substantial sequence differences between the oligonucleotide probe set sequences and the target DNA. Thus, if a gene is called "present" in one accession and "absent" in another accession, this indicates substantial differences in this gene's sequences between the two accessions. Approximately less than 1000 probe sets with sequences substantially varied among accessions were identified and eliminated from the further transcriptome scan analysis. Further analysis of these genes showed that the majority of them encoded transposon-related proteins, kinases, and disease-resistance proteins.

To determine the reproducibility of the comparative genomic hybridization experiments, the same genomic DNA was hybridized onto two different microarrays in parallel. Only a small fraction of genes showed hybridization signals with significant changes (greater than 2-fold) between the two replicated experiments: 0.4% from the Col-0 replicates and 0.2% from the Ler replicates. These results are similar to the results from reproducibility studies for RNA detection using the same GENECHIP® microarray (Zhu and Wang, 2000).

Comparability of gene expression profiles among accessions. Transcription profiles of different organs at different developmental stages were compared among the five accessions with the following strategy: (1) Only genes that were expressed in at least one RNA sample were selected for further analysis; (2) Since microarray hybridization detects the degree of sequence homology between the DNA probes and the hybridizing target nucleic acid molecules, as well as the abundance of the target molecules, the transcript abundance was normalized to the corresponding genomic DNA by dividing the average differences of genes from each organ by the average differences of genomic DNA of that particular accession. This was to exclude the possibility that the differences detected between accessions by RNA hybridization were caused by the differences at the DNA sequence level, rather than at the transcription level; and (3) The normalized MRNA expression values were used to calculate the Pearson correlation coefficient between all possible pairs of accessions (10 pairs, since we had 5 different accessions) for each gene, and were also used for cluster analysis (Eisen, M. B., Spellman, P. T., Brown, P. O., and Botstein, D. (1998) Cluster analysis and display of genome-wide expression patterns. Proc. Natl. Acad. Sci. USA 95, 14863-14868).

To validate gene expression variations detected by GENECHIP® microarray through heterologous hybridization, quantitative RT-PCR using accession-specific primers and probes was performed. A comparison of mRNA levels of 13903_at (At3g54050) and 17392_s_at (At3g53260) was performed, measured by GENECHIP® and quantitative RT-PCR in 18 different samples. In general, the quantitative RT-PCR results agreed with GENECHIP® microarray results, confirmed the expression differences of this gene between accessions Col-0 and C-24. However, the correlation coefficient between results of microarray and quantitative RT-PCR improved from 0.85 for 13903_at, and 0.88 for 17392_at (microarray data without genomic DNA normalization) to 0.91 (13903_at), and 0.90 (17392_at) (microarray data with genomic DNA normalization). This result supports our analysis strategy used for transcription analysis of different accessions, and indicates that genomic DNA normalization minimizes the interference from DNA sequence variations in transcription profiling of samples in different genetic backgrounds.

In addition, we have also validated mRNA expression levels of 12 genes, 7 of which did not show different expression levels, and 5 of which did show difference between the flowers of Col-0 as compared to Ler, detected from microarray experiments. The results from quantitative RT-PCR analysis are quite consistent with the data obtained from the microarray experiments following genomic DNA normalization, confirming that this strategy works well in the identification of gene expression polymorphism between different accessions. However, for some of the genes such as 17142_at, 16892_at, 17860_at, which showed no significant differences from GENECHIP® experiments, about 2-fold difference (17142_at: 2.05-fold, 16892_at: 2.17-fold, 17860_at: 2.26-fold) were detected by RT-PCR, suggesting that RT-CR might be more sensitive to GENECHIP® experiments, in terms of detecting differences in gene expression.

General Similarities of Transcriptional Profiles among Accessionsfrom Various Organs at Different Stages. Among the 6573 genes whose expression could be detected in at least one of the RNA samples, the expression patterns of most of the genes (5255) correlate well (r>0.5) in at least 5 pair-wise comparisons (yellow bars), indicating that the expression patterns for most genes from different accessions are similar. However, when we randomly permuted the RNA samples from the same organs of different accessions (see Materials and Methods for details), the number of genes whose expression does not correlate for each pair of accession comparison increased significantly from total number of 93 of the original data to 461, confirming that the high correlation among gene-expression profiles of different accessions did not occur completely by random chance.

The relations among the accessions based on the expression profiles were further analyzed by cluster analysis with the normalized gene-expression data. The overall relations among all samples confirmed that expression differences among the accessions were small, as evident by the finding that the gene-expression differences are greater across different organs of the same accession than across different accessions in the same organ. Two clusters, representing the two major evolutionary events in vascular plants, emerged from the experimental tree: a cluster of axis-origin organs, including roots and young seedlings, and a cluster from auxiliary organs, including vegetative leaves, flowers, and siliques (reproductive leaves) and the associated inflorescences. The axis cluster consists of roots from 2 different developmental stages, 2 weeks and 5 weeks, as well as 4-day-old seedlings, which are mainly composed of root tissues. The cluster of auxiliary organs can be further divided into two subclusters, a cluster for the vegetative leaves, and a cluster composed of organs originating from the reproductive leaves. Within an organ, especially for leaves, however, variations are contributed by both developmental differences and accession differences.

Accession-Specific Gene Expression during Development. Although C24 is the accession that was most similar to Col-0 in its protein-coding sequence and gene-expression patterns during most stages of development, cluster analysis detected significant differences between these two accessions in late development, such as 11-week old leaves, where C24 did not cluster with Col-0 anymore. To identify genes which represent the accession-difference between C24 and Col-0, and to differentiate them from the genes which could possibly reflect the difference at different developmental stages of these two accession plants at the same age and grown under the same conditions, we employed the statistical analysis of microarray data (SAM) developed by Tusher (Tusher, V. G., Tibshirani, R., and Chu, G. (2001) Significance analysis of microarrays applied to the ionizing radiation response. Proc. Natl. Acad. Sci. USA 98, 5116-21), with genomic DNA normalized expression data from 2-, 5- and 11-week old leaves of C24 and Col-0. Here we artificially treated samples from 2-, 5-, and 11-week old leaves as three biological replicates and compared the difference between Col-0 and C24.

Based on SAM, 35 genes were identified to potentially express differently between the leaves of C24 and Col-0, with a false discovery rate 4.9%. These genes were then functionally classified according to the MIPS functional classification. Besides those genes with unclassified functions, the top three categories contained genes with possible functions in primary metabolism, stress response and signaling. In addition, five genes encoding putative transcription factors, such as zinc-finger transcription factors, EREBP-1 were included within this group of 35 genes. In addition, five genes encoding signaling proteins such as kinases, auxin-induced proteins IAA9 were also included, suggesting the involvement of signal transduction pathways and the corresponding transcription events in differentiating these two different accessions.

Discussion. The *Arabidopsis* GENECHIP® microarray was used to study MRNA expression differences among different *Arabidopsis* accessions. Currently, the complete genome information and many tools for functional genomic studies in *Arabidopsis*, such as the GENECHIP® microarray, are available only for the most commonly used accession, Col-0. However, many genetic and molecular studies have been carried out using accessions other than Col-0. To facilitate the utilization of genomic information and tools in studies with other accessions, we developed a new strategy for analyzing genome-wide gene expression profiles by heterologous probe-target hybridization. We used genomic DNA hybridization signals as the reference for normalizing RNA hybridization signals, thus subtracting the sequence variations among different accessions from the gene-expression variations. Using this approach, genes with different expressions in accessions other than Col-0 could be readily identified, thereby broadening the application of the current GENECHIP® microarrays. A study reported previously in yeast to understand the genetic architecture of natural variation in gene expression linked 570 differentially expressed genes between two parental yeast strains, to one or more genetic markers, and further grouped these genes into two categories, the cis-acting modulators and trans-acting modulators. However, no genomic DNA normalization has been employed in this study.

Data from the comparative genomic hybridization of different accessions confirmed that the currently available GENECHIP® microarray, employing the method of the present invention, is suitable for transcription profiling of *Arabidopsis* accessions other than Col-0, since at least 97% of the probe set sequences could detect genes from the genomes of the five accessions we investigated. Only relatively small numbers of genes were observed in C24 (127 or 1.5%), Ler (292 or 3.4%), WS-2 (202 or 2.3%), and NO-0 (294 or 3.4%) that showed significant differences from Col-0 in from genomic DNA hybridization. This indicates that sequence variations in the gene-coding regions are small.

In summary, we developed a strategy to overcome the sequence barrier for comparison of gene expression profiles among closely related accessions or species. We further detected gene-expression variations in 20% of the 6573 genes that do not show significant variation in the probe sequence selected from their coding regions among the five *Arabidopsis* accessions most commonly used in molecular genetics studies. The results were confirmed by RT-PCR and data mining results. The gene expression variations among different *Arabidopsis* accessions may be caused by variations in gene-coding regions or in promoter regions. Using the approach of large-scale gene-expression profiling of different accessions, combined with genetic information, it is possible to identify putative gene-expression polymorphisms and to link these polymorphisms to the differential regulatory mechanisms, which were probably subjected to natural selection during evolution. This could further help in understanding genome and transcriptome dynamics during evolution (Gibson, G. (2002) Microarrays in ecology and evolution: a preview. Mol. Ecol. 11, 17-24) through constantly evaluating the fitness of existing DNA within the genome as well as the fitness of the gene-regulatory mechanisms by natural selection. Moreover, since phenotypic variation among different accessions probably reflects genetic variation that is important for the plant's adaptation to specific environmental conditions, transcriptome analysis, as a powerful tool for molecular phenotyping, should provide an alternative approach (in addition to QTL analysis) for studying the interaction between genetic variation and environment. This approach could be used to study functional variations among accessions and consequently to introduce the valuable variations into the germ plasm by conventional breeding, based on the information obtained from the study. This study sheds light on the field of plant evolutionary genomics by furthering our understanding of how different transcriptional regulatory mechanisms contribute to shaping the genome among different accessions.

In light of the detailed description of the invention and the examples presented above, it can be appreciated that the several aspects of the invention are achieved.

It is to be understood that the present invention has been described in detail by way of illustration and example in order to acquaint others skilled in the art with the invention, its principles, and its practical application. Particular formulations and processes of the present invention are not limited to the descriptions of the specific embodiments presented, but rather the descriptions and examples should be viewed in terms of the claims that follow and their equivalents. While some of the examples and descriptions above include some conclusions about the way the invention may function, the inventors do not intend to be bound by those conclusions and functions, but put them forth only as possible explanations.

It is to be further understood that the specific embodiments of the present invention as set forth are not intended as being exhaustive or limiting of the invention, and that many alternatives, modifications, and variations will be apparent to those of ordinary skill in the art in light of the foregoing examples and detailed description. Accordingly, this invention is intended to embrace all such alternatives, modifications, and variations that fall within the spirit and scope of the following claims. All references cited herein are incorporated by reference in their entirety.

What is claimed is:

1. A method of correcting oligo probe hybridization signals, the method comprising:
   (a) deriving a correction coefficient for an oligo probe using genomic DNA hybridizations to a first microarray, comprising:
      (i) measuring signals from each oligo probe during multiple genomic DNA hybridizations to the first microarray, wherein the multiple genomic DNA hybridizations are within a linear range; and
      (ii) calculating a correction coefficient for each oligo probe based on the measured signals from the genomic DNA hybridizations according to the equation $C_i = 1/S_i$, where $C_i$ is the correction coefficient and $S_i$ is the average of the signals for each probe observed in step (a)(i); and
   (b) correcting oligo probe hybridization signals from a second microarray for determining gene expression, comprising:
      (i) employing one or more of the oligo probes with calculated correction coefficients from (a) in the second microarray for determining gene expression; and
      (ii) correcting the signal for each oligo probe on the gene expression microarray using the calculated correction coefficient, wherein the corrected oligo probe hybridization signals derived from the gene expression microarray are outputted to a computer memory.

2. The method of claim 1 comprising calculating an average and standard deviation for signals from the genomic DNA hybridizations observed on each probe.

3. The method of claim 2 comprising determining an uncertainty coefficient for each oligo probe.

4. The method of claim 3 wherein the uncertainty coefficient is based on a ratio of the average to the standard deviation.

5. The method of claim 3 comprising deciding whether to redesign or disregard a probe having an uncertainty coefficient greater than a predetermined value.

6. The method of claim 5 wherein the predetermined value is approximately 1.0.

7. The method of claim 3 comprising using the corrected signal to calculate an expression level for a gene by:
   calculating a weighting factor for the oligo probe where if m ($\geq$=1) oligo probes are used to detect the expression level of the gene, w is the weighing factor, and d is the uncertainty coefficient, the weighting factor for the ith oligo probe can be calculated according to the formula:

$$w_i = \frac{d_i}{\sum_{i}^{m} d_i};$$

and
   calculating the expression level for a gene using the calculated weighing factor to determine the expression value v according to the formula:

$$v = 1/m \sum_{i=1}^{m} w_i S_i^{corrected}$$

where m is the number of the oligo probes used to detect the expression level of the gene and $S_i^{corrected}$ is the corrected signal based on the calculated correction coefficient.

8. A method of obtaining correction coefficients for probes, the method comprising:
   determining a dynamic range for genomic DNA binding by measuring a concentration signal curve;
   measuring signals from each probe during multiple hybridizations to a microarray with the genomic DNA within a linear range, wherein the linear range is based on the determination of the dynamic range;
   normalizing the signal intensities from the multiple hybridizations;
   calculating an average signal for each probe from the normalized signal intensities; and
   calculating a correction coefficient for each probe based on the measured signals from the genomic DNA hybridizations according to the equation $C_i = 1/S_i$, where $C_i$ is the correction coefficient and $S_i$ is the average signal for each probe from the normalized signal intensities, wherein the correction coefficients are outputted to a computer memory.

9. The method of claim 8 and further comprising calculating an average and standard deviation for signals from the genomic DNA hybridizations observed on each probe.

10. The method of claim 9 comprising determining an uncertainty coefficient for each oligo probe.

11. The method of claim 10 wherein the uncertainty coefficient is based on a ratio of the average to the standard deviation.

12. The method of claim 10 and further comprising deciding whether to redesign or disregard a probe having an uncertainty coefficient greater than a predetermined value.

13. The method of claim 12 wherein the predetermined value is approximately 1.0.

14. A computer implemented method of using correction coefficients for oligo probes, the method comprising:
   calculating a corrected signal for a probe according to the method of claim 1;
   calculating a weighting factor for a probe;
   calculating an expression level for a gene as a function of the weighting factor; and
   calculating an uncertainty of the gene expression.

15. The method of claim 14 and further comprising converting the corrected signal to a number of copies per cell.

16. The method of claim 15 and further comprising converting measurements of other genes to the number of copies per cell.

17. The method of claim 16 wherein the measurements of other genes are corrected based on a known number of copies per cell for a corrected signal.

18. The method of claim 14 wherein the weighting factor for a probe is proportional to an uncertainty coefficient associated with each probe.

19. The method of claim 18 wherein the weighting factor for a probe is equal to the uncertainty coefficient for the probe divided by the sum of uncertainty coefficients for all the probes for the gene.

20. The method of claim 14 wherein the expression level for a gene is the sum of weight times the corresponding corrected signal for the probes used to detect the gene divided by the number of probes used to detect the gene.

21. The method of claim 14 wherein the uncertainty of the gene expression level is based on the sum of the uncertainty coefficient for a probe times the corresponding corrected signal divided by the number of probes used to detect the gene.

22. The method of claim 14 wherein each probe has an associated uncertainty coefficient, and wherein the probe with the highest uncertainty is discarded prior to using the correction coefficients.

23. The method of claim 14 and further comprising making a call for the gene based on the uncertainty of the gene expression level.

24. The method of claim 23 wherein making a call further comprises:
    subtracting a background from the average intensities of probes;
    normalizing probe intensities globally;
    applying the correction coefficient to each probe; and
    determining a call based upon a Z-score for the gene.

25. The method of claim 23 wherein the call is made by a person.

26. A computer system comprising a processor to perform a method of using correction coefficients for oligo probes, the method comprising:
    calculating a corrected signal for a probe according to the method of claim 1;
    calculating a weighting factor for a probe;
    calculating an expression level for a gene as a function of the weighting factor; and
    calculating an uncertainty of the gene expression.

* * * * *